(12) United States Patent
Boman et al.

(10) Patent No.: US 7,591,997 B2
(45) Date of Patent: Sep. 22, 2009

(54) METHOD FOR DETERMINING THE SUSCEPTIBILITY OF A SUBJECT TO INFECTION

(75) Inventors: Hans G. Boman, Stockholm (SE); Mats Andersson, Stockholm (SE); Katrin Pütsep, Stockholm (SE); Göran Carlsson, Stockholm (SE)

(73) Assignee: Mabtech AB, Nacka (SE)

( * ) Notice: Subject to any disclaimer, the term of this patent is extended or adjusted under 35 U.S.C. 154(b) by 0 days.

(21) Appl. No.: 10/530,606

(22) PCT Filed: Oct. 10, 2003

(86) PCT No.: PCT/EP03/11240

§ 371 (c)(1),
(2), (4) Date: Feb. 21, 2006

(87) PCT Pub. No.: WO2004/034061

PCT Pub. Date: Apr. 22, 2004

(65) Prior Publication Data

US 2007/0059691 A1 Mar. 15, 2007

(30) Foreign Application Priority Data

Oct. 10, 2002 (GB) ................ 0223655.2

(51) Int. Cl.
*A61K 49/00* (2006.01)
*A61K 39/38* (2006.01)
*A61K 39/00* (2006.01)

(52) U.S. Cl. ............ 424/9.2; 424/9.1; 424/184.1; 424/185.1; 435/4; 435/7.1; 436/501; 530/300; 530/350

(58) Field of Classification Search ............ 424/9.1, 424/9.2, 184.1, 185.1; 436/501; 435/4, 7.1; 530/300, 350
See application file for complete search history.

(56) References Cited

U.S. PATENT DOCUMENTS

| 5,972,594 A | 10/1999 | Heine |
| 6,159,936 A | 12/2000 | Lehrer et al. |
| 2002/0072495 A1 | 6/2002 | Chertov et al. |
| 2003/0175755 A1 | 9/2003 | Abiko et al. |

FOREIGN PATENT DOCUMENTS

| DE | 100 28 725 A1 | 12/2001 |
| JP | 2001-288105 | 10/2001 |
| WO | WO 99/11663 | 3/1999 |
| WO | WO 99/13080 | 3/1999 |
| WO | WO 02/060468 A2 | 8/2002 |

OTHER PUBLICATIONS

Bals, et al., "Transfer of a Cathelicidin Peptide Antibiotic Gene Restores Bacterial Killing In a Cystic Fibrosis Xenograft Model," *J. Clin. Invest.*, 103(8):1113-1117, (1999).

Agerberth, et al., "The Human Antimicrobial and Chemotactic Peptides LL-37 and α-Defensins are Expressed by Specific Lymphocyte and Monocyte Populations," *Blood*, 96(9):3086-3093 (Nov. 1, 2000).

Bals, et al., "Augmentation of Innate Host Defense by Expression of a Cathelicidin Antimicrobial Peptide," *Infection and Immunity*, (67)11:6084-6089 (Nov. 1999).

Bals, R., "Epithelial Antimicrobial Peptides in Host Defense Against Infection," *Respiratory Research*, 1(3):141-150 (2000).

Baranova, et al., "Alkaline Phosphatase Activity in Neutrophils From Patients With Severe Congenital Neutropenia (Kostmann's Syndrome)," *International Journal of Hematology*, 70:236-240 (1999).

Boman, H., "Peptide Antibiotics and Their Role in Innate Immunity," *Annual Review of Immunology*, 13:61-92 (1995).

Borregaard N. and Cowland, J.B., "Granules of the Human Neutrophilic Polymorphonuclear Leukocyte," *Blood*, 89(10):3503-3521 (May 15, 1997).

Bülow, et al., "Sorting of Neutrophil-Specific Granule Protein Human Cathelicidin, hCAP-18, When Constitutively Expressed in Myeloid Cells," *Journal of Leukocyte Biology*, 72:147-153 (Jul. 2002).

Carlsson, G. and Fasth, A., " Infantile Genetic Agranulocytosis, Morbus Kostmann: Presentation of Six Cases From the Original "Kostmann Family" and a Review," *Acta. Pediatr.*, 90:757-764 (2001).

Dale, et al., "Localized Antimicrobial Peptide Expression in Human Gingiva," *Journal of Periodontal Research*, 36:285-294 (2001).

Defraia, E. and Marinelli, A., " Oral Manifestations of Congenital Neutropenia or Kostmann Syndrome," *The Journal of Clinical Pediatric Dentistry*, 26(1): 99-102 (2001).

Roester, et al., "In Vitro Functions of Neutrophils Induced by Treatment With rhG-CSF in Severe Congenital Neutropenia," *Eur. J. Haematol.*, 46:112-118 (1991).

Ganz, et al., "Microbicidal/Cytotoxic Proteins of Neutrophils Are Deficient in Two Disorders: Chediak-Higashi Syndrome and "Specific" Granule Deficiency," *J. Clin. Invest.*, 82:552-556 (Aug. 1988).

Gudmundsson, et al., "Structure of The Gene for Porcine Peptide Antibiotic PR-39, A Cathelin Gene Family Member: Comparative Mapping of The Locus for The Human Peptide Antibiotic FALL-39," *Proc. Natl. Acad. Sci., USA*, 92:7085-7089 (Jul. 1995).

Gudmundsson, et al., "The Human Gene FALL39 and Processing of The Cathelin Precursor to The Antibacterial Peptide LL-37 in Granulocytes," *Eur. J. Biochem.*, 238:325-332 (1996).

Guthmiller, et al., "Susceptibilities of Oral Bacteria and Yeast to Mammalian Cathelicidins," *Antimicrobial Agents and Chemotherapy*, 45(11):3216-3219 (Nov. 2001).

(Continued)

*Primary Examiner*—Rodney P. Swartz
(74) *Attorney, Agent, or Firm*—Hamilton, Brook, Smith & Reynolds, P.C.

(57) ABSTRACT

A method for determining the susceptibility of a subject to infection, which method comprises: (i) providing a sample from said subject; (ii) detecting any LL-37 present in said sample; (iii) optionally comparing the level of LL-37 in said sample to a control sample; and (iv) determining the susceptibility of said subject to infection, wherein no LL-37 or a low level of LL-37 indicates that said subject is susceptible to infection.

14 Claims, 3 Drawing Sheets

OTHER PUBLICATIONS

Huttner, K.M. and Bevins, C.L., "Antimicrobial Peptides as Mediators of Epithelial Host Defense," *Pediatric Research*, 45(6):785-794 1999).

Nagaoka, et al., "Synergistic Actions of Antibacterial Neutrophil Defensins and Cathelicidins," *Inflammation Research*, 49:73-79 (2000).

Slots, J., "*Actinobacillus actinomycetemcomitans* and *Porphyromonas gingivalis* in Periodontal Disease: Introduction," *Periodontology 2000*, 20:7-13 (1999).

Sørensen, et al., "An ELISA for hCAP-18, The Cathelicidin Present in Human Neutrophils and Plasma," *Journal of Immunological Methods*, 206:53-59 (1997).

Sørensen, et al., "Human Cathelicidin, hCAP-18, is Processed to The Antimicrobial Peptide LL-37 by Extracellular Cleavage With Proteinase 3," *Blood*, 97(12):3951-3959 (Jun. 15, 2001).

Tanaka, et al., "Sensitivity of *Actinobacillus actinomycetemcomitans* and Capnocytophaga spp. to The Bactericidal Action of LL-37: A Cathelicidin Found in Human Leukocytes and Epithelium," *Oral Microbiology and Immunology*, 15:226-231 (2000).

Turner, et al., "Activities of LL-37, a Cathelin-Associated Antimicrobial Peptide of Human Neutrophils," *Antimicrobial Agents and Chemotherapy*, 42(9):2206-2214 (Sep. 1998).

Van Dyke, T.E. and Vaikuntam, J., "Neutrophil Function and Dysfunction in Periodontal Disease," *Current Opinion in Periodontology*, pp. 19-27 (1994).

van Winkelhoff, et al., "Microbiology of Destructive Periodontal Disease in Adolescent Patients With Congenital Neutropenia," *Journal of Clinical Periodontology*, 27:793-798 (2000).

Zasloff, M., "Antimicrobial Peptides of Multicellular Organisms," *Nature*, 415:389-395 (Jan. 24, 2002).

Koczulla, R., et al., "An Angiogenic Role for the Human Peptide Antibiotic LL-37/hCAP-18," *J. Clinical Investigation*, 111(11):1665-1672 (2003).

Mosca, D. R., et al., "IB-367, a Protegrin Peptide with In Vitro and In Vivo Activities Against the Microflora Associated with Oral Mucositis," *Antimicrobial Agents and Chemotherapy*, 44(7):1803-1808 (2000).

Gombart, et al., "Neutrophil-Specific Granule Deficiency: Homozygous Recessive Inheritance of a Frameshift Mutation in the Gene Encoding . . . ", *Blood*, 97(9):2561-2567 (May 1, 2001).

Weinberg, et al., "Epithelial Antimicrobial Peptides: Review and Significance for Oral Applications", *Critical Reviews in Oral Biology and Medicine*, 9(4):399-414 (Nov. 11, 1998).

Nizet, et al., "Innate Antimicrobial Peptide Protects the Skin from Invasive Bacterial Infection", *Nature*, 414:454-457 (Nov. 22, 2001).

Zetterström, R., "Kostmann Disease—Infantile Genetic Agranulocyctosis: Historical Views and New Aspects", *Acta Paeditrica*, 91(12):1279-1281 (1992).

Pütsep, et al., "Deficiency of Antibacterial Peptides in Patients with Morbus Kostmann: An Observation Study", *The Lancet*, 360(9340):1144-1149 (Oct. 12, 2002).

Ong, et al., "Endogenous Antimicrobial Peptides and Skin Infections in Atopic Dermatitis", *N. Engl. J. Med.*, 347(15):1151-1160 (Oct. 10, 2002).

Jurevic, et al., "Single-Nucleotide Polymorphisms and Haplotype Analysis in β-Defensin Genes in Different Ethnic Populations", *Genetic Testing*, 6(4):261-269 (2002).

Lehrer, R. I. and Ganz, T., "Cathelicidins: A Family of Endogenous Antimicrobial Peptides", *Current Opinion in Hematology*, 9(1): 18-22 (Jan. 2002).

Levy, O., "Antimicrobial Proteins and Peptides of Blood: Templates for Novel Antimicrobial Agents", *Blood*, 96(8):2664-2672 (Oct. 15, 2000).

Cirioni, O. et al., "Efficacy of LL-37 and Granulocyte Colony-Stimulating Factor in a Neutropenic Murine Sepsis Due to *Pseudomonas aeruginosa,*" *Shock*, 30(4): 443-448 (2008).

METHOD FOR DETERMINING THE SUSCEPTIBILITY OF A SUBJECT TO INFECTION

RELATED APPLICATIONS

This application is the U.S. National Stage of International Application No. PCT/EP2003/011240, filed 10 Oct. 2003, published in English, and claims priority under 35 U.S.C. § 119 or 365 to Great Britain Application No. 0223655.2, filed 10 Oct. 2002.

FIELD OF THE INVENTION

The present invention relates to diagnosis of neutropenia and to methods for determining susceptibility to infection. The invention also relates to methods of treating neutropenia and of treating and/or preventing infection.

BACKGROUND TO THE INVENTION

All animals and plants produce antibacterial peptides, which are major effector molecules of innate immunity. More than 700 antibacterial peptides are known. Antibacterial peptides are natural bactericidal components that are similar in potency to classical antibiotics.

All antibacterial peptides from animals are gene encoded and the primary transcript is translated into an inactive precursor that needs proteolytic processing to become a bactericidal effector. The use of an inactive precursor is thought to protect the host cells from damage and may be an important regulatory mechanism.

In humans, antibacterial peptides are produced at all body surfaces by epithelial cells, specialized granular cells and white blood cells. Most species have families of several rather similar peptides, each with their own genes. This is thought to be an evolutionary safeguard against deleterious mutations. Two major families of the human repertoire of antibacterial peptides are the α- and β-defensins. Granulated cells such as Paneth cells and neutrophils produce α-defensins while β-defensins are mainly produced by epithelial cells. LL-37, encoded by the CAMP gene is the only cathelicidin type peptide that has been identified in humans. LL-37 is produced by neutrophils and to a lesser extent by peripheral lymphocytes. Skin and gingiva also express LL-37. The proform of LL-37 is cathelin-LL-37 which is cleaved, for example upon neutrophil excitation, to release the bactericidal peptide LL-37.

Morbus Kostmann is a severe congenital neutropenia here defined as the disease in descendants of the original Kostmann family. Morbus Kostmann arises as a result of a recessive mutation and differs from most other inherited neutropenia which are thought to be due to dominant mutations in the gene for elastase. The origin of the autosomal recessive neutropenia morbus Kostmann is not known. The undefined gene defect(s) results in a neutrophil maturation arrest at the promyelocyte/myelocyte stage.

The Kostmann syndrome was fatal up to around 1975 when modern antibiotics were introduced. Since around 1990, when recombinant granulocyte colony stimulating factor (G-CSF) became available, an improved treatment with recombinant human G-CSF has been practiced. This involves daily injections of G-CSF combined with antibiotic therapy when necessary. The G-CSF treatment restores the number of neutrophils to normal levels and this has dramatically improved the quality of life for these patients. However, in spite of the corrected neutrophil levels, Kostmann patients are still prone to infections and suffer from severe periodontal disease.

SUMMARY OF THE INVENTION

The present inventors have shown that G-CSF treated morbus Kostmann patients have normal numbers of neutrophils in the circulation, but these cells lack at least one bactericidal effector molecule, LL-37 and its precursor cathelin-LL-37. The inventors have thus demonstrated that to combat infections and to control the normal flora in neutropenia, it is crucial to maintain both the number of neutrophils in the circulation and their proper equipment in terms of antimicrobial effectors. The present inventors have also demonstrated that levels of the antibacterial peptide LL-37 may be reduced in humans and have surprisingly shown that the reduction in the level of this single antimicrobial peptide increases susceptibility to bacterial infections.

In particular, the present inventors have shown that a reduction in the levels of LL-37 in the saliva and neutrophils results in an increased susceptibility to periodontal diseases which are polymicrobial infections caused mainly by bacteria from the normal oral flora.

Accordingly, the present invention provides:
a method for determining the susceptibility of a subject to infection, which method comprises:
  (i) providing a sample from said subject;
  (ii) detecting any LL-37 present in said sample;
  (iii) optionally comparing the level of LL-37 in said sample to a control sample; and
  (iv) determining the susceptibility of said subject to infection, wherein no LL-37 or a low level of LL-37 indicates that said subject is susceptible to infection;
a method of treating an individual to reduce the risk of infection comprising administering to a subject susceptible to infection an amount of LL-37 effective to reduce susceptibility to infection;
a method for determining the susceptibility of an individual to infection and treating the individual to reduce the risk of infection, the method comprising:
  (i) providing a sample from a subject;
  (ii) detecting any LL-37 present in said sample;
  (iii) optionally comparing the level of LL-37 in said sample to a control sample;
  (iv) determining the susceptibility of said subject to infection, wherein no LL-37 or a low level of LL-37 indicates that said subject is susceptible to infection; and
  (v) administering to a subject susceptible to infection an amount of an antimicrobial agent effective to reduce susceptibility to infection;
Use of LL-37 in the manufacture of a medicament for the prophylactic treatment of infection.
Use of LL-37 in the manufacture of a medicament for the treatment of infection in a subject having neutropenia.
a method of diagnosing neutropenia in a subject, which method comprises:
  (i) providing a sample from said subject;
  (ii) detecting any LL-37 present in said sample;
  (iii) optionally comparing the level of LL-37 in said sample to a control sample; and
  (iv) determining whether said subject has neutropenia, wherein no LL-37 or a low level of LL-37 indicates that said subject has neutropenia.

a method of determining whether a subject having neutropenia has a type of neutropenia associated with reduced levels of LL-37, which method comprises:
  (i) providing a sample from said subject;
  (ii) detecting any LL-37 present in said sample;
  (iii) optionally comparing the level of LL-37 in said sample to a control sample; and
  (iv) determining whether said subject has a type of neutropenia associated with reduced levels of LL-37, wherein no LL-37 or a low level of LL-37 indicates that said subject has a type of neutropenia associated with reduced levels of LL-37.

a method of treating a subject having neutropenia, which method comprises:
  (i) providing a sample from said subject;
  (ii) detecting any LL-37 present in said sample;
  (iii) optionally comparing the level of LL-37 in said sample to a control sample;
  (iv) determining whether said subject has neutropenia, wherein no LL-37 or a low level of LL-37 indicates that said subject has neutropenia; and
  (v) administering a therapeutically effective amount of an agent suitable for the treatment of neutropenia to a subject having neutropenia.

a method of treating a subject having neutropenia, which method comprises administering to a subject in need thereof a therapeutically effective amount of LL-37.

use of LL-37 in the manufacture of a medicament for the treatment of neutropenia.

a product comprising LL-37 and a cytostatic drug, corticosteroid or growth factor for separate, sequential or simultaneous use in the treatment of the human or animal body.

use of LL-37 in the manufacture of a medicament for the treatment of infection in a subject receiving or who has received a cytostatic drug, corticosteroid or growth factor.

BRIEF DESCRIPTION OF THE SEQUENCE LISTING

Figure 1:
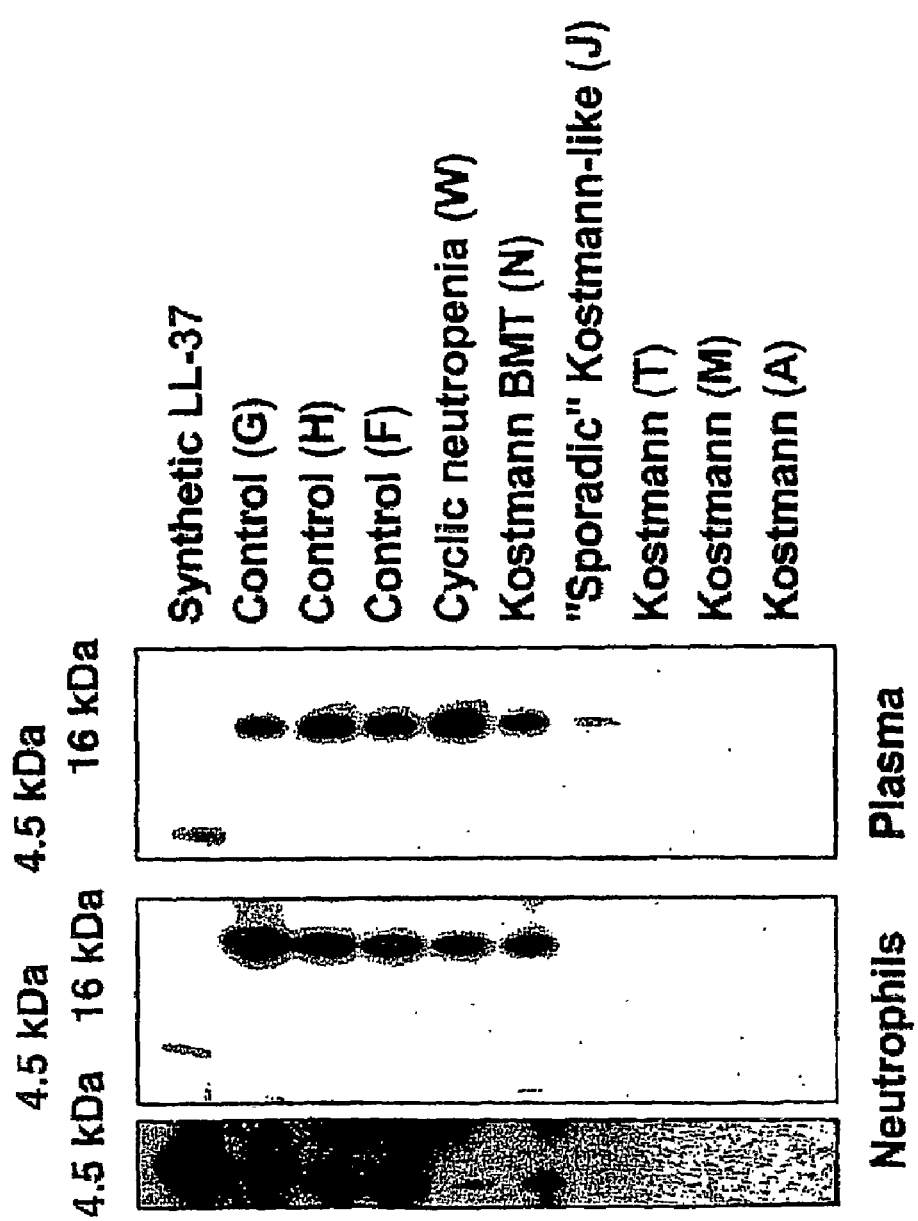
FIG. 1 shows a western blot analysis of LL-37 (4·5 kDa) and cathelin-LL-37 (16 kDa) in neutrophils (left and middle part) and plasma (right part). Samples are from Kostmann patients (A, M, T, N), one Kostmann-like patient (3) and one cyclic neutropenia (W). Healthy controls are: one unrelated (G), a brother (H) and the mother (F) of (A). The same neutrophil blot is shown on the left and in the middle, but the exposure time was 100 times longer in the left part. With the longer exposure time the area of the cathelin-LL-37 band was all black and for clarity is not shown. Neutrophil extracts (5000 cells/well (approximately 15 μg protein)) were separated on 10-20% SDS-PAGE, blotted onto PVDF membranes, and detected with anti-LL-37 antibody. Plasma samples (2 ill representing 25-50 μg protein) were analyzed similarly.

SEQ ID NO: 1 is the cDNA sequence encoding the proform (or precursor) of LL-37.
SEQ ID NO: 2 is the amino acid sequence of the proform of LL-37.
SEQ ID NO: 3 is the amino acid sequence of LL-37.
SEQ ID NO: 4 is the amino acid sequence of a fragment of the propart of the proform of LL-37 used to generate antibodies to the proform of LL-37.

DETAILED DESCRIPTION OF THE INVENTION

Method of Determining Susceptibility to Infection

The present invention provides an in vitro method for determining the susceptibility of a subject to infection by detecting LL-37 levels in a sample from a subject. LL-37 levels are typically correlated with susceptibility to infection such that a lower level of LL-37 is indicative of a higher susceptibility to infection. To determine whether a subject has increased susceptibility to infection compared to a normal individual, the levels of LL-37 in a sample from a subject can be compared to the levels of LL-37 in a sample from a normal subject.

The method for determining the susceptibility of a subject to infection consists essentially of the following steps:
  (i) providing a sample from said subject;
  (ii) detecting any LL-37 present in said sample; and
  (iii) optionally comparing the level of LL-37 in said sample to a control sample; and
  (iv) determining the susceptibility of said subject to infection, wherein no LL-37 or a low level of LL-37 indicates that said subject is susceptible to infection.

An increased susceptibility to infection may also result when normal levels of LL-37 are expressed but the expressed LL-37 is dysfunctional, i.e. the expressed LL-37 has no antibacterial activity. The present invention provides a method for determining susceptibility to infection wherein the level of functional LL-37 is detected. Thus, in one embodiment, the method comprises determining whether the LL-37 detected comprises a mutation that renders it dysfunctional.

The subject is generally a human. The subject may be male or female. The subject may be suffering from a disease that affects the production or function of white blood cells, for example neutropenia. The subject may be one that has been or is being treated with a corticosteroid or cytostatic drug. The subject may be being treated with immunosuppressants. The subject may be an individual who suffers from recurrent infections. The subject may be exposed to or be about to be exposed to a risk of infection. For example, the subject may be about to undergo a surgical operation such as dental surgery, the subject may have burn injuries and/or the subject may be a diabetic.

The level of LL-37 in the sample is generally the concentration of LL-37. The level of LL-37 may alternatively be taken to be the amount of LL-37 in a sample of a given size. To determine whether an individual is more or less susceptible to infection than normal it is necessary to compare the level of LL-37 in a sample from a subject to the level in a control sample.

The levels of LL-37 in the sample may be determined by comparing the results of an assay for detecting LL-37 in the sample to the results of the assay carried out on a standard sample. The standard sample may contain a known amount of LL-37, such as recombinant LL-37.

The control sample may typically be a similar sample from a normal subject. The normal subject is typically a healthy subject. A healthy subject is one not suffering from an infection, particularly an infection of the type the susceptibility to which is being determined. Preferably the normal individual is not immunosuppressed, is not being treated with a cytostatic drug or corticosteroid and is not suffering from a disease that affects the production or function of white blood cells, such as neutropenia.

The sample from a control subject used to determine the level of LL-37 is typically similar to the sample from the subject being tested in that it is a sample of the same type, for example both are saliva samples. Preferably the samples from the control and test subjects are taken at the same time of day.

Alternatively, the control sample may be a general reference value. For example, the control sample may be a theoretical sample from a reference database showing LL-37 levels of the general population or from a smaller group of individuals, e.g. race or family, of which the subject is a member. Such databases may easily be built up over time. Preferably the control LL-37 level to which the LL-37 level in a sample from the subject is compared is the mean level from the selected group of individuals.

Thus in one embodiment the control sample is from a normal subject or is representative of the level of LL-37 in a normal subject and step (iii) comprises determining whether the level of LL-37 in said sample is raised or lowered compared to the level of LL-37 in the control sample and, in step (iv), a lowered level of LL-37 indicates that said subject is susceptible to infection.

A sample taken from a subject being susceptible to infection may contain no LL-37 or less than 70%, for example less than 60%, less than 50% or less than 40%, and preferably contains less than 30%, for example less than 20% or less than 10% of the amount of LL-37 found in a sample taken from a normal subject.

The control sample to which the levels of LL-37 in the individual under test are compared may be a sample from another subject having reduced levels of LL-37. The control sample may be a theoretical sample from a reference database of such subjects. Preferably the control value is a range of reduced levels of LL-37 found in subjects who are susceptible to infection. In this case a subject being susceptible to infection is a subject having the same or similar level to the control sample.

In one aspect, the control sample may be taken from the subject under test at an earlier time point. For example, where the subject is or has been immunosuppressed the sample under test may be compared to a sample from the same subject before he/she was immunosuppressed.

The infection may be infection by any microbe against which LL-37 is effective or forms part of the host defence. Preferably the infection is a bacterial infection. The bacteria causing the infection may be, for example, *Staphyllococci, Streptococci E. coli* or *Salmonella*. Preferably, the bacterial infection is an *Actinobacillus actinomycetemcomitans* infection.

The infection may be of any part of the body, for example, the mouth, eye, lung, skin, nose, sinus, throat, ear, urinary tract, gastrointestinal tract or vagina. Preferably, the infection is an oral infection such as gingivitis and/or periodontitis.

Administration of corticosteroids may result in a reduced susceptibility to infection. Accordingly, an assay of the invention may be used to determine whether too much or too little corticosteroid is being administered to a patient.

Method for Preventing Infection

Also provided by the present invention are methods for treating an individual to reduce the risk of infection comprising administering to a subject susceptible to infection an amount of LL-37 effective to reduce susceptibility to infection. A subject susceptible to infection may be identified using a method of the invention.

In a preferred aspect the subject is one about to be exposed to a risk of infection. For example, the subject may be about to undergo a surgical procedure, such as dental surgery.

In one aspect the present invention provides a method for determining the susceptibility of an individual to infection and treating the individual to reduce the risk of infection, the method comprising:
  (i) providing a sample from a subject;
  (ii) detecting any LL-37 present in said sample;
  (iii) optionally comparing the level of LL-37 in said sample to a control sample;
  (iv) determining the susceptibility of said subject to infection, wherein no LL-37 or a low level of LL-37 indicates that said subject is susceptible to infection; and
  (v) administering to a subject susceptible to infection an amount of an antimicrobial agent or agent which enhances synthesis of an. antimicrobial agent effective to reduce susceptibility to infection.

The control sample may be from a normal subject and step (iii) comprises determining whether the level of LL-37 in said sample is raised or lowered compared to the level of LL-37 in the control sample and, in step (iv), a lowered level of LL-37 indicates that said subject is susceptible to infection.

An amount of an antimicrobial agent effective to reduce susceptibility to infection is an amount that will attack an infection-causing microbe entering the body such that so that no symptoms or less severe symptoms of infection by the microbe are observed. An effective amount of an agent which enhances synthesis of an antimicrobial agent is an amount that results in expression of an amount of the antimicrobial agent effective to reduce susceptibility to infection.

Preferably, the antimicrobial agent is LL-37. Other suitable antimicrobial agents may be used and include analogues of LL-37 and classical antibiotics.

Preferably the agent which enhances synthesis of an antimicrobial agent enhances the synthesis of LL-37 and may be, for example, butyric acid.

LL-37 may be administered as the proform of LL-37 (cathelin-LL-37) or as the mature form of LL-37. Administration of the proform of LL-37 is advantageous because it does not cause tissue damage. Alternatively, a nucleic acid, such as a mRNA or cDNA sequence, preferably in an expression vector, encoding either the proform of LL-37 or the mature form of LL-37 may be administered. An enzyme capable of cleaving the proform of LL-37 to the mature form of LL-37, or a nucleic acid encoding such an enzyme, may be co-administered with the proform of LL-37.

The use of LL-37 in the manufacture of a medicament for use in the prophylactic treatment of infection is also provided.

Method for Treating Infection

The present inventors have shown, for the first time that LL-37 may be particularly effective in the treatment of infections in subjects with neutropenia. Accordingly the invention provides the use of LL-37 in the manufacture of a medicament for use in the treatment of infection in a subject having neutropenia.

A method for the treatment of infection in a subject having neutropenia generally comprises administering to a subject having neutropenia a therapeutically effective amount of LL-37. Any suitable form of LL-37 as described herein may be administered. A therapeutically effective amount is an amount which will kill the microbes causing the infection such that the symptoms of the infection are reduced and or the condition of the patient is alleviated.

The present inventors have also shown for the first time that patients having gingivitis and periodontitis are deficient in LL-37 and therefore that LL-37 may be of particular benefit in the treatment of gingivitis and/or periodontitis. Accordingly the invention provides the use of LL-37 in the manufacture of a medicament for use in the treatment of gingivitis and/or periodontitis.

A method for the treatment of gingivitis and/or periodontitis generally comprises administering to a subject having gingivitis and/or periodontitis a therapeutically effective amount of LL-37. Any suitable form of LL-37 as described herein may be administered. A therapeutically effective amount is an amount which will kill the bacteria causing gingivitis and/or periodontitis such that the symptoms of gingivitis and/or periodontitis are reduced, the damage caused by the infection is prevented from worsening and/or the condition of the patient is alleviated.

Method of Determining Type of Neutropenia

The present invention also provides a method for determining whether a subject having neutropenia has a type associated with reduced levels of LL-37. Also provided by the invention is a method for determining whether a type of neutropenia is associated with reduced levels of LL-37.

A method of determining whether a subject having neutropenia has a type of neutropenia associated with reduced levels of LL-37, typically comprises:
 (i) providing a sample from said subject;
 (ii) detecting any LL-37 present in said sample;
 (iii) optionally comparing the level of LL-37 in said sample to a control sample; and
 (iv) determining whether said subject has a type of neutropenia associated with reduced levels of LL-37, wherein no LL-37 or a low level of LL-37 indicates that said subject has a type of neutropenia associated with reduced levels of LL-37.

The subject is generally a human and may be male or female. The subject may have been diagnosed as having neutropenia by any suitable means. Typically neutropenia may be diagnosed by cytological examination. The subject having neutropenia may have been treated for their neutropenia, for example by treatment with a growth or differentiation factor such as G-CSF. Preferably, a subject having neutropenia and being treated for neutropenia has symptoms suggesting that the subject is susceptible to infection.

The level of LL-37 in the sample is generally the concentration of LL-37. The level of LL-37 may alternatively be taken to be the amount of LL37 in a sample of a given size. To determine whether an individual has a type of neutropenia associated with reduced levels of LL-37 it is necessary to compare the level of LL-37 in a sample from a subject to the level in a control sample.

The control sample is typically a similar sample from a normal subject. A normal subject is generally a subject not having neutropenia but may be a subject having a type of neutropenia not associated with reduced LL-37 levels. The subject not having neutropenia is preferably a subject that is not immunosupressed and/or that is not suffering from any infection. The sample from an individual not having neutropenia used to determine the level of LL-37 is similar to the sample from the subject being tested in that it is a sample of the same type, for example both are saliva samples. Preferably the samples from the control and test subjects are taken at the same time of day.

Alternatively, the control sample may be a general reference value. For example, the control sample may be a theoretical sample from a reference database showing LL-37 levels of the general population or from a smaller group of individuals, e.g. race or family, of which the subject is a member. Such databases may easily be built up over time. Preferably the control LL-37 level to which the LL-37 level in a sample from the subject is compared is the mean level from the selected group of individuals.

Thus in one embodiment, the control sample is a sample from a normal subject or is representative of the level of LL-37 in a sample from a normal subject, step (iii) comprises determining whether the level of LL-37 in said sample is raised or lowered compared to the level of LL-37 in the control sample and, in step (iv), a lowered level of LL-37 indicates that said subject has a type of neutropenia associated with reduced levels of LL-37.

The control sample to which the levels of LL-37 in the individual under test are compared may be a sample from another subject having reduced levels of LL-37, for example another subject having a type of neutropenia associated with reduced LL-37 levels, preferably morbus Kostmann. The control sample may be a theoretical sample from a reference database of such subjects. The mean reduced level of LL-37 is used as the control value. Preferably, the control value is a range of LL-37 levels associated with that type of neutropenia. In this case a subject having a type of neutropenia associated with reduced LL-37 levels is a subject having the same or similar level to the control sample.

A subject diagnosed as having a type of neutropenia associated with reduced levels of LL-37 is a subject having a lower level of LL-37 compared to the level of LL-37 from a subject not having neutropenia. A sample taken from a subject having a type of neutropenia associated with reduced levels of LL-37 may contain no LL-37. Alternatively, a sample taken from a subject having a type of neutropenia associated with reduced levels of LL-37 may contain less than 70%, for example less than 60%, less than 50% or less than 40%, and preferably contains less than 30%, for example less than 20% or less than 10% of the amount of LL-37 found in a control sample from a normal subject or a representative value therefor.

There are many types of neutropenia. Any type of neutropenia associated with reduced levels of LL-37 may be diagnosed using a method of the invention. Types of neutropenia that may be associated with reduced levels of LL-37 include is sporadic neutropenia, Kostmann morbus, peripheral neutropenia, primary splenic neutropenia, periodic neutropenia, congenital neutropenia and chronic hypoplastic neutropenia. Preferably, the type of neutropenia diagnosed using a method of the invention is Kostmann morbus.

A method for determining whether a type of neutropenia is associated with reduced levels of LL-37, similarly comprises:
 (i) providing a sample from a subject having neutropenia;
 (ii) detecting any LL-37 present in said sample;
 (iii) optionally comparing the level of LL-37 in said sample to a control sample; and
 (iv) determining whether the type of neutropenia that the subject has is a type associated with reduced levels of LL-37, wherein no LL-37 or a low level of LL-37 in said sample indicates that the type of neutropenia that the subject has is a type associated with reduced levels of LL-37.

Where the control sample is a sample from a subject not having neutropenia, step (iii) may comprise determining whether the level of LL-37 in said sample is raised or lowered compared to the level of LL-37 in the control sample and, in step (iv), a lowered level of LL-37 typically indicates that said subject has a type of neutropenia associated with reduced levels of LL-37.

Method for Diagnosing Neutropenia

The present invention provides an in vitro method for the diagnosis of neutropenia by detecting LL-37 levels in a sample from a subject. LL-37 levels are typically lowered in a subject having neutropenia compared to a subject not having neutropenia. The method for determining whether an individual has neutropenia consists essentially of the following steps:

(i) providing a sample from said subject;
(ii) detecting any LL-37 present in said sample;
(iii) optionally comparing the level of LL-37 in said sample to a control sample; and
(iv) determining whether said subject has neutropenia, wherein no LL-37 or a low level of LL-37 indicates that said subject has neutropenia.

The subject is generally a human. The subject may be male or female. The subject typically shows increased susceptibility to infections and may have a history of recurrent infections.

The level of LL-37 in the sample is generally the concentration of LL-37. The level of LL-37 may alternatively be taken to be the amount of LL-37 in a sample of a given size. To determine whether an individual has neutropenia it is necessary to compare the level of LL-37 in a sample from a subject to the level in a control sample. The control sample is typically a similar sample from a subject not having neutropenia. The subject not having neutropenia is preferably a subject that is not immunosuppressed and/or that is not suffering from any infection. The sample from an individual not having neutropenia used to determine the level of LL-37 is similar to the sample from the subject being tested in that it is a sample of the same type, for example both are saliva samples. Preferably the samples from the control and test subjects are taken at the same time of day.

Alternatively, the control sample may be a theoretical sample from a reference database showing LL-37 levels of the general population or from a smaller group of individuals, e.g. race or family, of which the subject is a member. Such databases may easily be built up over time. Preferably the control LL-37 level to which the LL-37 level in a sample from the subject is compared is the mean level from the selected group of individuals.

Thus in one embodiment, the control sample is a sample from a subject not having neutropenia, step (iii) comprises determining whether the level of LL-37 in said sample is raised or lowered compared to the level of LL-37 in the control sample and, in step (iv), a lowered level of LL-37 indicates that said subject has neutropenia.

The control sample to which the levels of LL-37 in the individual under test are compared may be a sample from another subject having reduced levels of LL-37, for example another subject having neutropenia, preferably Kostmann morbus. The control sample may be a theoretical sample from a reference database of such subjects. The mean reduced level of LL-37 is used as the control value. Preferably, the control value is a range of LL-37 levels associated with neutropenia. In this case a subject having neutropenia is a subject having the same or similar level to the control sample.

A subject diagnosed as having neutropenia is a subject having a lower level of LL-37 compared to the level of LL-37 from a subject not having neutropenia. A sample taken from a subject having neutropenia may contain no LL-37. Alternatively, a sample taken from a subject having neutropenia may contain less than 70%, for example less than 60%, less than 50% or less than 40%, and preferably contains less than 30%, for example less than 20% or less than 10% of the amount of LL-37 found in a control sample taken from a normal subject.

Method of Treating Neutrogenia

Also provided by the present invention are methods for treating neutropenia. In one aspect a method of treating neutropenia comprises:

(i) providing a sample from a subject;
(ii) detecting any LL-37 present in said sample;
(iii) optionally comparing the level of LL-37 in said sample to a control sample;
(iv) determining whether said subject has neutropenia, wherein no LL-37 or a low level of LL-37 indicates that said subject has neutropenia; and
(v) administering a therapeutically effective amount of an agent suitable for the treatment of neutropenia to a subject having neutropenia.

Where the control sample is a sample from a subject not having neutropenia, step (iii) may comprise determining whether the level of LL-37 in said sample is raised or lowered compared to the level of LL-37 in the control sample and, in step (iv), a lowered level of LL-37 typically indicates that said subject has a type of neutropenia neutropenia associated with reduced levels of LL-37.

Any agent useful in the treatment of neutropenia may be administered. Preferably the agent is a growth factor, more preferably G-CSF or GM-CSF. Preferably the agent is LL-37 or an analogue of LL-37. LL-37 may be administered as the proform of LL-37 (cathelin-LL-37) or as the mature form. Alternatively a nucleic acid, such as a mRNA or cDNA sequence, preferably in an expression vector, encoding either the proform of LL-37 or the mature form of LL-37 may be administered. An enzyme capable of cleaving the proform of LL-37 to the mature form of LL-37, or a nucleic acid encoding such an enzyme, may be co-administered with the proform of LL-37. LL-37 and the growth-factor, preferably G-CSF or GM-CSF, may be co-administered.

Also provided is a method of treating a subject known to have neutropenia, which method comprises administering to a subject in need thereof a therapeutically effective amount of LL-37. The use of LL-37 in the manufacture of a medicament for the treatment of neutropenia is also provided by the invention.

A method for the treatment of neutropenia generally comprises administering to a subject having neutropenia a therapeutically effective amount of LL-37. Any suitable form of LL-37 as described herein may be administered. A therapeutically effective amount is an amount which will reduce one or more symptom of the disease or generally alleviate the condition of the patient.

Combination Therapy

The present invention provides a product comprising LL-37 and a cytostatic drug, LL-37 and a corticosteroid or LL-37 and a growth differentiation factor for separate, sequential or simultaneous use in the treatment of the human or animal body. The product is useful in the treatment of any disease that may be treated using the cytostatic agent, corticosteroid or growth/differentiation factor. Such diseases include neutropenia, malignant diseases and inflammatory diseases such as ulcerative colitis and Crohn's disease. Patients with bone marrow transplants may also be treated using the product. In such treatments the amount of LL-37 administered in combination with the corticosteroid or cytostatic agent is an amount effective to counteract the side effects of the corticosteroid or cytostatic agent.

Suitable cytostatic agents include 5-Fluoracil, Methotrexate, Cytarabin, Daunorubicin, Bleomycin, Mitomycin C and Cis-platinum.

Suitable corticosteroids include cortisone, hydrocortisone, prednisolone, methylprednisolone, triamcinolone, dexamethasone, paramethasone and betamethasone.

Preferably the growth/differentiation factor is G-CSF or GM-CSF. Administration of G-CSF or GM-CSF and LL-37 is particularly advantageous in the treatment of neutropenia.

LL-37 may be administered as the proform of LL-37 (cathelin-LL-37) or as the mature form of LL-37. An analogue of LL-37 may be administered. Administration of the proform of LL-37 is advantageous because it is incapable of causing tissue damage. Alternatively, a nucleic acid, such as a mRNA or cDNA sequence, preferably in an expression vector, encoding either the proform of LL-37 or the mature form of LL-37 may be administered. An enzyme capable of cleaving the proform of LL-37 to the mature form of LL-37, or a nucleic acid encoding such an enzyme, may be co-administered with the proform of LL-37.

Also provided by the invention is the use of LL-37 in the manufacture of a medicament for the treatment or prevention of infection in a subject who is about to receive, who is receiving or who has received a cytostatic drug, corticosteroid or growth factor.

Accordingly a method of treating a disease selected from neutropenia, malignant diseases and inflammatory diseases is also provided. A method of treating a bone-marrow transplant patient is also provided. The method typically comprises administering to a subject in need thereof, a therapeutically effective amount of a cytostatic agent or corticosteroid and an amount of LL-37 effective to reduce susceptibility to infection. A therapeutically effective amount of a cytostatic agent or corticosteroid is an amount which will reduce one or more symptoms of the disease or generally alleviate the condition of the patient. An amount of LL-37 effective to reduce susceptibility to infection is an amount that will attack an infection-causing microbe entering the body such that so that no symptoms or less severe symptoms of infection by the microbe are observed.

Sample

A sample used in any one of the methods of the invention typically comprises a bodily fluid of the individual and may be obtained by any suitable method, for example by using a swab, such as a mouth swab. The sample may be a blood, urine, saliva or cheek cell sample.

The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of blood or other sample.

LL-37

The LL-37 detected in any one of the methods of the invention may be the proform of LL-37 (cathelin-LL-37) or the mature form of LL-37. Alternatively LL-37 mRNA may be detected. In one embodiment a degradation product of LL-37 may be detected.

Detecting

In any one of the methods of the invention, LL-37 may be detected using any suitable assay. Typically LL-37 may be detected using an agent, preferably an antibody, which is capable of specifically binding to the proform and/or the mature form of LL-37. A suitable assay format is the ELISA assay. Western blotting, flow cytometry (FACS) or mass spectrophotometry may also be used. These techniques are well known to a person skilled in the art.

An antibody suitable for use in a detection method is generally one that binds specifically to LL-37. An antibody, or other agent, "specifically binds" to LL-37 when it binds with preferential or high affinity to LL-37 but does not substantially bind, does not bind or binds with only low affinity to other polypeptides. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments which bind LL-37. Such fragments include Fv, F(ab') and F(ab')2 fragments, as well as single chain antibodies. Furthermore, the antibodies and fragment thereof may be chimeric antibodies, CDR-grafted antibodies or humanised antibodies.

Where LL-37 mRNA is detected, a probe or primer that hybridises to the mRNA sequence may be used in a detection method. The probe or primer typically has a sequence complementary to the mRNA sequence but may contain one or more mismatch providing that under the hybridising conditions used in the assay, the probe or primer binds specifically to the LL-37 mRNA. A probe or primer "specifically binds" to LL-37 mRNA when it binds with preferential or high affinity to LL-37 mRNA but does substantially bind, does not bind or binds with only low affinity to other mRNA sequences.

Administration

The formulation of any of the therapeutic agents mentioned herein will depend upon factors such as the nature of the agent and the condition to be treated. Any such agent may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. A physician will be able to determine the required route of administration for each particular patient.

For the treatment of gingivitis and/or periodontitis, LL-37 or an analogue thereof may be formulated in a toothpaste or mouthwash. Accordingly, a toothpaste comprising LL-37, or an analogue thereof, and a mouthwash comprising LL-37, or an analogue thereof are also provided by the invention.

Typically the agent is formulated for use with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective amount of agent is administered. The dose may be determined according to various parameters, especially according to the agent used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

Nucleic acid encoding an LL-37 may be administered to the mammal in a method of gene therapy. Nucleic acid, such as RNA or DNA, and preferably, DNA, is provided in the form of a vector, such as the which may be expressed in the cells of the subject.

Nucleic acid encoding the polypeptide may be administered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 µg nucleic acid for particle mediated gene delivery and 10 µg to 1 mg for other routes.

The following Examples illustrate the invention.

EXAMPLES

Example 1

Detection of LL-37

Using an antibody directed against LL-37, we analysed neutrophil extracts and plasma samples by Western blot from all four morbus Kostmann patients now alive.

Patients and Controls

All four Kostmann patients were diagnosed before the age of 5 months and with typical clinical findings. Two additional and unrelated patients with congenital neutropenia were included in the study: one with a more mild form of Kostmann-like syndrome (she was 5 years of age at diagnosis and was referred because of chronic gingivitis) and one with cyclic neutropenia. All patients had periodontitis before G-CSF treatment started, except for the patient with cyclic neutropenia, though these patients can suffer also from this affliction. Out of 22 controls, 19 were relatives and 3 were unrelated healthy individuals. The patients, their relatives and one healthy control donated their blood at the Pediatric Ward of Sunderby hospital, Luleå, Sweden. Ethical permission was granted.

Blood Cell Separation and Extraction

Coagulation of whole blood was prevented by EDTA. Neutrophils were enriched by density centrifugation through Ficoll-Paque Plus (Amersham Pharmacia Biotech AB, Sweden). The top layer (plasma) was collected and frozen at −80° C. Lymphocytes were collected from the interface, washed in phosphate-buffered saline (PBS) and frozen at −80° C. The bottom cell fraction, containing mainly granulocytes and red blood cells, was collected and the erythrocytes lysed for 2 min with distilled water. Remaining cells were diluted with PBS and washed 3 times in PBS and stored at −80° C.

Protein content in the samples was determined by the BCA protein assay kit (Pierce, USA).

Antisera and Western Blot Analysis

Affinity purified rabbit anti-peptide antibodies (Inovagen, Sweden) were made against two synthetic peptides, the whole mature LL-37 peptide and a peptide segment from in the cathelin propart (AVLRAMDGINQRSSD (SEQ ID NO: 4), accession no. Z38026.1).

Plasma and extracts from neutrophils respectively were mixed with sample buffer and heated at 90° C. for 3 min. Proteins were separated on a 10-20% Tris-Tricine SDS-acrylamide gel (Novex) and blotted onto PVDF-filters (Novex). The filters were blocked for 1 h with 5% milk powder in PBS/0.1% Tween 20 (PBST). Filters were washed and incubated over night with anti-LL-37 antibody 1:10 000 dilution and after washing with secondary anti-rabbit serum coupled to HRP (BioRad) for 1 h in PBST. After additional washings, detection was by chemiluminescence using ECL plus (Amersham Pharmacia Biotech AB, Sweden). When the anti-cathelin-peptide antibody was used, the samples were reduced in 5% 2-mercaptoethanol (80° C. / 10 min) before electrophoretic separation.

Results

The antibody recognises both the 4.5 kDa mature LL-37 and the 16 kDa unprocessed precursor, cathelin-LL-37. Both precursor and mature LL-37 could be detected in the three controls as shown in FIG. 1. Because the signal for the mature LL-37 was so much weaker than the precursor, we had to overexpose the neutrophil filter to detect the 4.5 kDa band, (FIG. 1, left part). An additional 17 controls out of which 16 were relatives were tested giving the same results.

FIG. 1 (middle part) shows clearly that the Kostmann patients A, M and T in their neutrophils were almost deficient in cathelin-LL-37. No LL-37 could be detected in these three patients (FIG. 1, left part). The bone marrow transplanted Kostmann patient (N) had close to normal levels of precursor and clearly detectable amounts of LL-37. In addition to "the original family members", one patient (J) diagnosed as a mild "sporadic" Kostmann-like syndrome (unrelated to the original family) had reduced level of cathelin-LL-37 compared to the controls (FIG. 1 middle part). In contrast, the patient diagnosed as cyclic neutropenia (W) had normal levels of cathelin-LL-37. The neutrophil blots were evaluated by densitometric readings. We estimated (FIG. 1 middle part) that the ratio of the 16 kDa precursor to the mature 4.5 kDa LL-37 in the controls exceeded 100/1.

Although neutrophil counts may vary with time, plasma level of cathelin-LL-37 is normally present in concentrations around 1.2 µg/ml. Our Western blot analysis (Figure 1, right part) shows that the patients T, M and A had 1-2% of normal plasma levels of cathelin-LL-37, estimated by densiometric scanning. The sporadic patient (J) had a 5-10-fold higher level than the Kostmann patient (which equals 10% of controls) and the transplanted patient (N) had close to normal levels (70% of controls). The same pattern of cathelin-LL-37 in patients and controls was obtained in Western blot analysis with an antibody directed against the cathelin part of the precursor. No free LL-37 could be detected in any of the samples even after a prolonged exposure.

Example 2

Detection of Defensins

The defensin content of the neutrophil extracts was quantified by analytical HPLC.

HPLC Analysis of Granulocyte Extracts

Peptides/proteins from the neutrophil enriched cell preparation were extracted in 30% acetic acid for 2.5 h at +4° C. and centrifuged. The supernatant was lyophilized and resuspended in 0.1% trifluoroacetic acid and centrifuged. The clear supernatant was analysed by analytical HPLC using a C18 column (Vydac, 218TP54, The Separation group, Hesperia, USA) and acetonitrile/water gradients from 10-60%. The elution position of defensins (HNP 1-3) was identified by matrix-assisted laser desorption/ionization time-of-flight (MALDI-TOF) mass spectrometry using a Reflex III (Bruker Daltronics, Germany). The peak area under the curve was calculated, translated to µg using purified defensin HNP 1 standard curves, compensated for the difference in loading and finally related to number of neutrophils and presented as µg of defensin/ $10^6$ neutrophil. HNP-1 was kindly donated by Dr.R. Lehrer, UCLA, USA.

Results

Kostmann patients had around 30% of the mean defensin content of the controls (per $10^6$ neutrophils) while the transplanted patient (N) and the patient with cyclic neutropenia (W) had relatively normal levels (Table 1).

Example 3

Neutrophil Turnover

Neutrophils have at least three different types of granules that can be fractionated by density centrifugations. Lactoferrin is produced by neutrophils and stored in the same secondary granules as cathelin-LL-37. The plasma levels of lactoferrin can, therefore, be used as an indicator of the turnover of neutrophils and as a marker for secondary granules development. We used an ELISA assay for recording the lactoferrin content of the plasma and correlated this to the neutrophil counts.

Assay for Lactoferrin

Lactoferrin was determined by a sandwich ELISA. Briefly, microtiter wells (Maxisorp, Nunc) were coated overnight with a monoclonal antibody against lactoferrin (Hy-test, Turko, Finnland). The plates were washed and samples added. A second polyclonal rabbit anti-lactoferrin (DAKO-immunoglobulins a/s, Glostrup, Denmark) and an alkaline phosphatase-conjugated polyclonal goat anti-rabbit antibody (DAKO-immunoglobulins a/s, Glostrup, Denmark) detected lactoferrin.

Results

No significant differences in lactoferrin levels between patients and controls were found (Table 1).

Example 4

Antibacterial Mechanism

To investigate the functionality of the neutrophils in the neutopenia patients, enriched neutrophils from the four Kostmann patients (A, M, T and N) were studied for the antibacterial mechanism, phagocytosis dependent oxidative burst.

Assay for Oxidative Burst

Oxidative burst was recorded by the Fc OxyBURST Green assay reagent according to manufacturers instructions (Molecular Probe, USA). In this case the blood was collected in heparinised tubes, pre-sedimented on dextrane prior to Ficoll-Paque separation and the remaining erythrocytes were lysed 2×30 sec with ice-cold distilled water and then resuspended in HBSS containing 5 mM glucose. Before the oxidative burst assay, 100 µl of PBS at 37° C. containing 1.5 mM $Mg^{2+}$ and 1.0 mM $Ca^{2+}$ was added, then the oxidative burst reagent at a final concentration of 75 µg/ml.

Results

Figure 2:
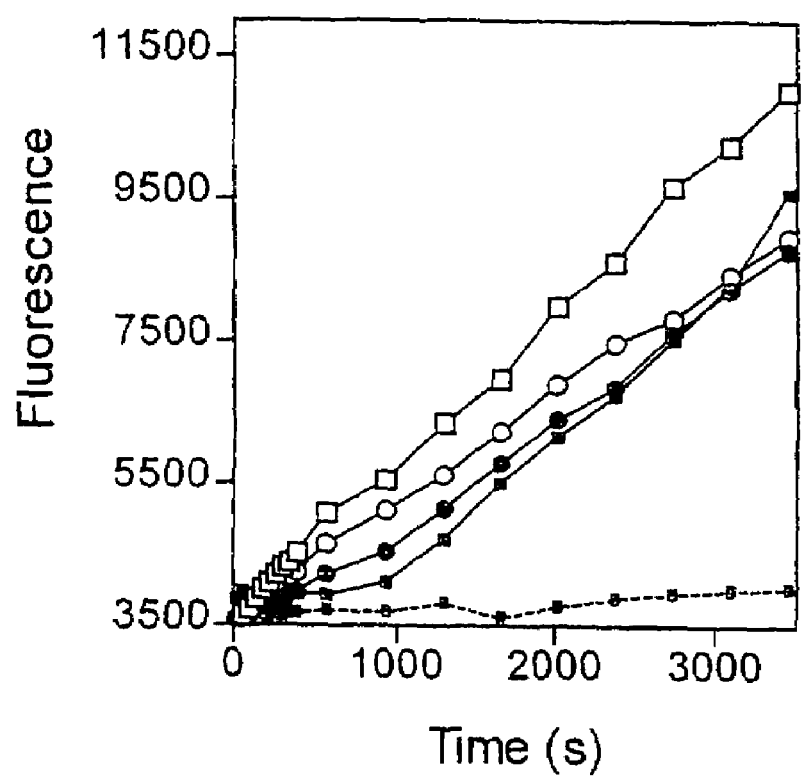
FIG. 2 shows the levels of oxidative burst of human neutrophils from Kostmann patients (A=□, M=○), one patient with cyclic neutropenia (●) and a healthy donor (■). The assay records Fc dependant internalisation of a covalent complex of rabbit polyclonal anti-BSA and BSA with a fluorescence probe. The dotted line represents background fluorescence.

FIG. 2 show that cells from two Kostmann patients (A and M) have comparable activity to one control and the cyclic neutropenia patient. There is, therefore, no evidence for any malfunction in this antibacterial mechanism. In addition, it is known that patients with severe neutropenia have normal or higher levels of alkaline phosphatase activity indicating the development of tertiary granules. This has also been observed for three of our patients.

Example 5

Activity of LL-37

Patients A, M and T have all periodontal problems, which for the treated Kostmann patients is an early affliction and becomes more severe as they age. The Gram-negative bacterium *A. actinomycetemconmitans* was abundant in patient (A), and at the age of 22 she has lost 50-75% of the bone in her front teeth. She also has gingivitis in the same part of the gum. Her 21 year old brother does not exhibit any of these symptoms.

Bacterial Strains and Microbial Assays

In this study we used an isolate of *Actinobacillus actinomycetemcomitans* from the oral cavitas of patient (A), kindly provided by Dr A. Johansson (Umeå). Bacteria were routinely grown on tryptic soy agar (Difco) supplemented with 0.5% yeast extract (TSBY) at microaerophilic conditions. The effect of LL-37 on *A. actinomycetemcomitans* was tested in a standard colony forming units (CFU)-assay (Tanaka et al., *Oral Microbiol Immunol.* 2000;15(4):226-31) by incubating $10^5$ bacteria for 90 min with 20 µg/ml of synthetic LL-37 in 10 mM phosphate buffer pH 7.2 with 1% TSBY.

Results

When tested in vitro, we found that synthetic LL-37 could stop the growth of the bacteria *A. actinomycetemcomitans* isolated from patient (A). In a standard assay bacteria treated with 20 µg/ml LL-37 for 90 min showed a 3-4 log reduction in colony counts.

Example 6

Detection of LL-37 in Saliva

With the findings of Example 5 in mind we investigated saliva samples by Western blot analysis for LL-37 and cathelin-LL-37.

Saliva Samples and Western Blotting

Unstimulated whole saliva was collected by spitting in Eppendorf tubes and frozen on dry ice. After melting they were centrifuged to remove cells/debris and used in further analysis. Protein content in the samples was determined by the BCA protein assay kit (Pierce, USA).

Saliva samples were mixed with sample buffer and western blotting was carried out as described above.

Figure 3:
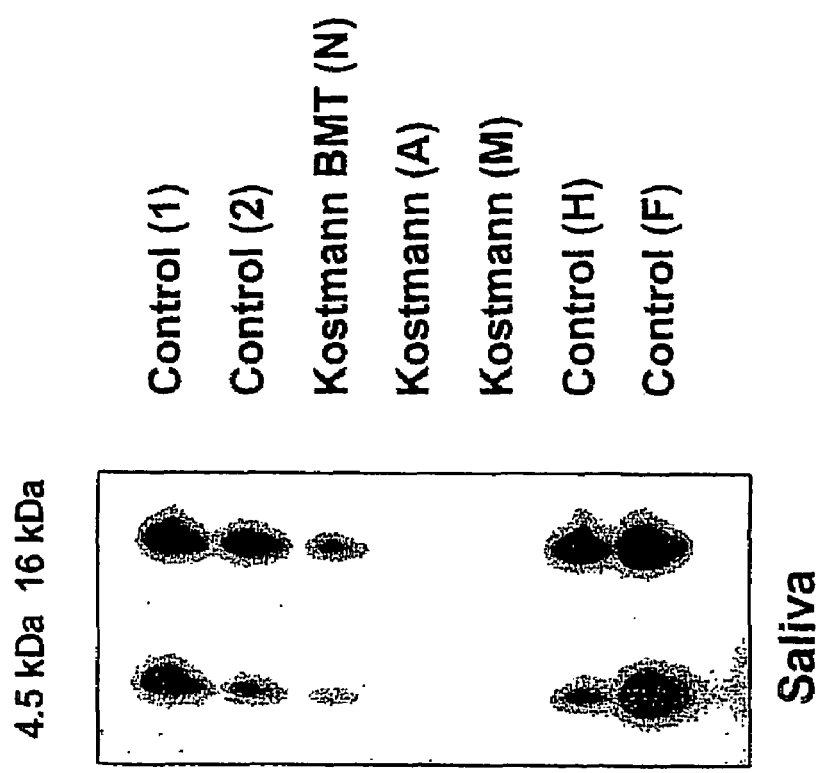
FIG. 3 shows the results of western blot analysis of saliva samples (0.5-1.5 μg protein) from Kostmann patients and different controls. The technical details are the same as for FIG. 1. One unrelated healthy male (1) and one female (2) served as additional controls. Kostmann patients and their relatives are designated as in FIG. 1 and Table 1.

Results FIG. 3 shows that the two Kostmann patients (A and M) were deficient in both the precursor cathelin-LL-37 and the effector molecule LL-37. Controls had high levels of both cathelin-LL-37 and LL-37 while the transplanted patient (N) had close to normal levels. The presence of peptides in saliva of patients and controls correlated with the presence of peptides in plasma. Saliva samples from controls and patients where collected at the same time of the day.

These results demonstrate that the antimicrobial peptide LL-37 normally is present as a defence molecule in the saliva, but that patients with morbus Kostmann lack the peptide both in saliva and in their neutrophils. The levels of LL-37 in the saliva thus correlate well to the oral health of the patients. It is likely that the absence of LL-37 gives growth advantage to *A. actinomycetenicomitans* resulting in a perturbed microflora in the gingival pocket and subsequent gingivitis.

TABLE 1

Kostmann patients and controls investigated

| Subject Genotype | Diagnosis | SEX | Born | ANC[1] | PBL[1] | Dental[2] problem | Lactoferrin Abs 405 nm/ 10 min | Defensin[3] µg/10⁶ neutrophils |
|---|---|---|---|---|---|---|---|---|
| A (K/K) | Kostmann | F | 1976 | 1.6[4] | 3.2 | +++ | 0.598 | 0.5 |
| M (K/K) | Kostmann | M | 1993 | 4.5[4] | 4.5 | + | 0.435 | 0.4 |
| T (K/K) | Kostmann | F | 1983 | 4.0 | 4.0 | ++ | 0.446 | 0.4 |
| N (+/3K) | Kostmann, BM transplated | M | 1984 | 4.0 | 2.3 | − | 0.254 | 0.8 |
| J (unknown) | Sporadic Kostmann | F | 1982 | 4.5 | 4.5 | (+) | 0.312 | 0.2 |
| W | Cyclic neutropenia | F | 1986 | 3.1 | 1.7 | − | 0.290 | 0.8 |
| H, Brother | Control | M | 1991 | 2.7 | 2.7 | − | 0.338 | 0.9 |
| F, Mother (+/K) | Control | F | 1969 | 2.8 | 2.8 | − | 0.323 | 1.3 |
| G, unrelated | Control | M | 1948 | 3.1 | 3.1 | − | 0.257 | 1.8 |

Patients A, M, N, T and controls are designated as in figures. Homozygotes are indicated as (K/K), the hetrozygote (+/K), the bone marrow transplanted with father as the donor (+/3K). Patient J is a mild Kostmann-like neutropenia unrelated to the original family.
[1]ANC designate absolute neutrophil counts performed by the clinical laboratory at Sunderby hospital. Before treatment ANC is <0.2 × 10⁹. PBL is peripheral blood lymphocytes.
[2]Dental problem are (+), +, ++ and +++ stands for increasing degree of gingivitis towards periodontitis. Absence of dental problems are noted as −.
[3]The values of defensin HNP 1-3 were calculated from analytical HPLC.
[4]Indicates activated cell morphology as judged by the laboratory at Sunderby hospital.

The invention claimed is:

1. A method for determining the susceptibility of a subject to infection, which method comprises:
   (i) providing a sample from said subject;
   (ii) detecting any LL-37 present in said sample;
   (iii) comparing the level of LL-37 in said sample to a control sample from a normal subject; and
   (iv) determining the susceptibility of said subject to infection, wherein no LL-37 or a lowered level of LL-37 compared to the level of LL-37 in said control sample indicates that said subject has an increased susceptibility to infection.

2. A method according to claim 1 wherein the infection is a bacterial infection.

3. A method according to claim 2 wherein said bacterial infection is an *Actinobacillus actinomycetemcomitans* infection.

4. A method according to claim 1 wherein said infection is an oral infection.

5. A method according to claim 4 wherein said oral infection is periodontitis.

6. A method according to claim 1 wherein said LL-37 is the proform of LL-37.

7. A method according to claim 1 wherein said LL-37 is the mature form of LL-37.

8. A method according to claim 1 wherein said subject is being treated or has been treated using a cylostatic drugs and/or a corticosteriod.

9. A method of diagnosing neutropenia in a subject, which method comprises:
   (i) providing a sample from said subject;
   (ii) detecting any LL-37 present in said sample;
   (iii) comparing the level of LL-37 in said sample to a control sample from a normal subject; and
   (iv) determining whether said subject has neutropenia, wherein no LL-37 or a lowered level of LL-37 compared to the level of LL-37 in said control sample indicates that said subject has neutropenia.

10. A method according to claim 9, wherein the neutropenia is morbus Kostmann.

11. A method of determining whether a subject having neutropenia has a type of neutropenia associated with reduced levels of LL-37, which method comprises:
   (i) providing a sample from said subject;
   (ii) detecting any LL-37 present in said sample;
   (iii) comparing the level of LL-37 in said sample to a control sample from a normal subject; and
   (iv) determining whether said subject has a type of neutropenia associated with reduced levels of LL-37, wherein no LL-37 or a lowered level of LL-37 compared to the level of LL-37 in said control sample indicates that said subject has a type of neutropenia associated with reduced levels of LL-37.

12. A method of treating a subject having neunopenia, which method comprises:
   (i) providing a sample from said subject;
   (ii) detecting any LL-37 present in said sample;
   (iii) comparing the level of LL-37 in said sample to a control sample from a normal subject;
   (iv) determining whether said subject has neutropenia, wherein no LL-37 or a lowered level of LL-37 compared to the level of LL-37 in the control sample indicates that said subject has neutropenia; and
   (v) administering a therapeutically effective amount of an agent suitable for the treatment of neutropenia to a subject having neutropenia.

13. A method according to claim 12 wherein said agent is LL-37.

14. A method of treating a subject having neutropenia, which method comprises administering to a subject in need thereof a therapeutically effective amount of LL-37.

* * * * *

UNITED STATES PATENT AND TRADEMARK OFFICE
CERTIFICATE OF CORRECTION

PATENT NO.        : 7,591,997 B2
APPLICATION NO. : 10/530606
DATED             : September 22, 2009
INVENTOR(S)       : Boman et al.

It is certified that error appears in the above-identified patent and that said Letters Patent is hereby corrected as shown below:

Column 21, Line 47, delete "cylostatic" and insert --cytostatic--

Column 22, Line 38, delete "neunopenia" and insert --neutropenia--

Signed and Sealed this

Twenty-second Day of December, 2009

David J. Kappos
*Director of the United States Patent and Trademark Office*

SEQUENCE LISTING

<160> NUMBER OF SEQ ID NOS: 4

<210> SEQ ID NO 1
<211> LENGTH: 615
<212> TYPE: DNA
<213> ORGANISM: homo sapiens
<220> FEATURE:
<221> NAME/KEY: CDS
<222> LOCATION: (12)..(614)

<400> SEQUENCE: 1

```
gaattccggc c atg aag acc caa agg aat ggc cac tcc ctg ggg cgg tgg        50
             Met Lys Thr Gln Arg Asn Gly His Ser Leu Gly Arg Trp
               1               5                  10 tca ctg gtg ctc ctg ctg ctg ggc ctg gtg atg cct ctg gcc atc att        98
Ser Leu Val Leu Leu Leu Leu Gly Leu Val Met Pro Leu Ala Ile Ile
    15                  20                  25 gcc cag gtc ctc agc tac aag gaa gct gtc ctt cgt gct ata gat ggc       146
Ala Gln Val Leu Ser Tyr Lys Glu Ala Val Leu Arg Ala Ile Asp Gly
30                  35                  40                  45 atc aac cag cgg tcc tcg gat gct aac ctc tac cgc ctc ctg gac ctg       194
Ile Asn Gln Arg Ser Ser Asp Ala Asn Leu Tyr Arg Leu Leu Asp Leu
                50                  55                  60 gac ccc agg ccc acg atg gat ggg gac cca gac acg cca aag cct gtg       242
Asp Pro Arg Pro Thr Met Asp Gly Asp Pro Asp Thr Pro Lys Pro Val
```

-continued

```
                65                  70                  75
agc ttc aca gtg aag gag aca gtg tgc ccc agg acg aca cag cag tca    290
Ser Phe Thr Val Lys Glu Thr Val Cys Pro Arg Thr Thr Gln Gln Ser
        80                  85                  90 cca gag gat tgt gac ttc aag aag gac ggg ctg gtg aag cgg tgt atg    338
Pro Glu Asp Cys Asp Phe Lys Lys Asp Gly Leu Val Lys Arg Cys Met
95                  100                 105 ggg aca gtg acc ctc aac cag gcc agg ggc tcc ttt gac atc agt tgt    386
Gly Thr Val Thr Leu Asn Gln Ala Arg Gly Ser Phe Asp Ile Ser Cys
110                 115                 120                 125 gat aag gat aac aag aga ttt gcc ctg ctg ggt gat ttc ttc cgg aaa    434
Asp Lys Asp Asn Lys Arg Phe Ala Leu Leu Gly Asp Phe Phe Arg Lys
                130                 135                 140 tct aaa gag aag att ggc aaa gag ttt aaa aga att gtc cag aga atc    482
Ser Lys Glu Lys Ile Gly Lys Glu Phe Lys Arg Ile Val Gln Arg Ile
            145                 150                 155 aag gat ttt ttg cgg aat ctt gta ccc agg aca gag tcc tag tgt gtg    530
Lys Asp Phe Leu Arg Asn Leu Val Pro Arg Thr Glu Ser
        160                 165                 170 ccc tac cct ggc tca ggc ttc tgg gct ctg aga aat aaa cta tga gag    578 caa ttt caa aaa aaa aaa aaa aaa aaa acc gga att c                  615
```

<210> SEQ ID NO 2
<211> LENGTH: 170
<212> TYPE: PRT
<213> ORGANISM: homo sapiens

<400> SEQUENCE: 2

```
Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

Arg Ser Ser Asp Ala Asn Leu Tyr Arg Leu Leu Asp Leu Asp Pro Arg
50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170
```

<210> SEQ ID NO 3
<211> LENGTH: 37
<212> TYPE: PRT
<213> ORGANISM: homo sapiens

<400> SEQUENCE: 3

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 4
<211> LENGTH: 15
<212> TYPE: PRT
<213> ORGANISM: homo sapiens

<400> SEQUENCE: 4

Ala Val Leu Arg Ala Ile Asp Gly Ile Asn Gln Arg Ser Ser Asp
1               5                   10                  15
```